(12) United States Patent
Bischof et al.

(10) Patent No.: US 8,110,960 B2
(45) Date of Patent: Feb. 7, 2012

(54) ELECTROMOTOR WITH A STATOR HAVING COOLING CONDUITS

(75) Inventors: Thomas Bischof, Illerbeuren (DE); Karl Mack, Leutkirch (DE); Dieter Werner, Leutkirch (DE)

(73) Assignee: SycoTec GmbH & Co. KG, Leutkirch im Allgäu (DE)

( * ) Notice: Subject to any disclaimer, the term of this patent is extended or adjusted under 35 U.S.C. 154(b) by 355 days.

(21) Appl. No.: 12/314,820

(22) Filed: Dec. 17, 2008

(65) Prior Publication Data

US 2009/0160269 A1 Jun. 25, 2009

(30) Foreign Application Priority Data

Dec. 20, 2007 (DE) .......................... 10 2007 062 541

(51) Int. Cl.
*H02K 9/00* (2006.01)
(52) U.S. Cl. .................... 310/227; 310/216.119; 310/52
(58) Field of Classification Search .................... 310/54, 310/57, 64, 216.119, 225, 227
See application file for complete search history.

(56) References Cited

U.S. PATENT DOCUMENTS

| 4,547,687 | A * | 10/1985 | Arai ................................. 310/58 |
| 6,425,761 | B1 * | 7/2002 | Eibofner ......................... 433/131 |
| 6,819,016 | B2 * | 11/2004 | Houle et al. ..................... 310/52 |
| 6,960,851 | B2 * | 11/2005 | Poulin et al. .................... 310/52 |
| 6,992,411 | B2 * | 1/2006 | Houle et al. ..................... 310/52 |
| 7,211,919 | B2 * | 5/2007 | Kalsi et al. ............. 310/216.113 |
| 2004/0012272 | A1 * | 1/2004 | Houle et al. ..................... 310/54 |
| 2005/0035673 | A1 * | 2/2005 | Lafontaine et al. .............. 310/58 |
| 2005/0067904 | A1 * | 3/2005 | Houle et al. ..................... 310/54 |

FOREIGN PATENT DOCUMENTS

| DE | 297 17 128 | 11/1997 |
| DE | 197 57 605 | 6/1999 |
| DE | 10 2006 005 316 | 8/2007 |
| EP | 0 627 804 | 12/1994 |
| WO | WO 2004/010559 | 1/2004 |

* cited by examiner

*Primary Examiner* — Quyen Leung
*Assistant Examiner* — Naishadh Desai
(74) *Attorney, Agent, or Firm* — Jacobson Holman PLLC

(57) ABSTRACT

An electromotor including a rotor rotatably running on bearings on a rotor shaft and a stator surrounding the rotor. The stator has a short-circuit body and a winding which can be impinged by current. The short-circuit body receives at least partly the medium line(s).

15 Claims, 4 Drawing Sheets

ELECTROMOTOR WITH A STATOR HAVING COOLING CONDUITS

BACKGROUND OF THE INVENTION

Figure 1:
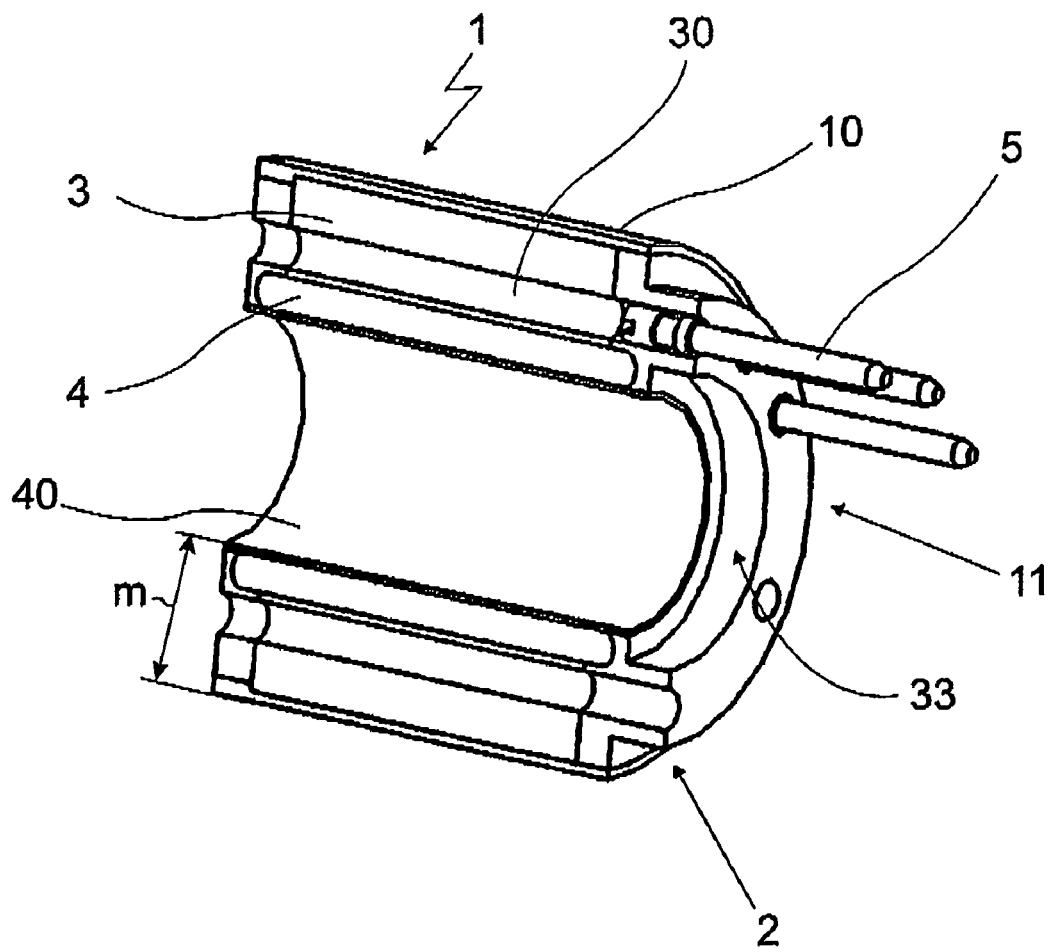

The invention refers to an electromotor comprising a rotor rotatably running on bearings on a rotor shaft and a stator surrounding the rotor, the stator having a short-circuit body and a winding which can be impinged by current and the electromotor having at least one medium line.

Electromotors of this type are employed for example for driving rotating dental or medical instruments. For this purpose the rotating instruments, for example drills or the like, are put on the electromotor via a standard coupling. The dental instrument has to be supplied during employment with different supply media via one or more medium lines. For example, in the dental field of employment spray air, spray water, cooling air, current, light and so on are required which have to be supplied through the electromotor to the driven dental instruments in the tool head. The medium lines have, of course, a certain diameter and have to be integrated in the area of the motor, where, as it is known, corresponding dental instruments as hand-held instruments are not supposed to exceed certain exterior dimensions, in order to not impair operating and handling. At the same time the electromotor, however, has to provide a sufficient turning moment and number of rotations.

In the state of the art several solutions have been known showing a passage of a medium line through the short-circuit body of a motor. All solutions of the state of the art which have become known comprise here solutions which deal exclusively with cooling of the motor or the short-circuit body.

SHORT ABSTRACT OF THE INVENTION

Coming from this state of the art it is an object of the present invention to provide an electromotor which finds a clever passage of the medium line(s) through the electromotor where the characteristics of the electromotor are not impaired much.

In order to solve this problem the invention comes from an electromotor as described in the beginning and suggests that the short-circuit body receives at least one passage for the at least partly building or receiving of the medium line or medium lines for passing one or more media. Depending on the case of application of the electromotor according to the invention one or even more medium lines have to be guided through the electromotor. The short-circuit body, present anyway because of the way the electromotor works, is now additionally employed for receiving the medium line(s) for the passage of the media through the motor. By integrating the medium line(s) in the short-circuit body the arrangement of the medium line(s) does not require additional constructive space, the influences of the medium line(s) on the magnetic qualities can also be neglected when the medium line(s) is/are arranged cleverly, which leads to almost unchanged characteristic numbers of the electromotor according to the invention. Vice versa, however, this means also that the constructive space gained by integrating the medium line in the short-circuit body can added to the stator or the winding at the stator, and thus the electromotor according to the invention offers improvement of its characteristic numbers, while the external dimensions of the subject according to the invention remain the same compared with the subject according to the state of the art.

In contrast to all solutions known in the state of the art it is not provided in the present solution according to the invention to employ the media guided through the short-circuit body, for example, at the motor itself, for example for cooling, but it is actually a solution where medium lines required for example at a tool driven by the motor are successfully guided through the motor without or only with a small loss of performance for the motor. Here it is possible to engage the medium line or medium lines from the one side with a motor, namely with the passage through the motor, the medium line itself is then formed, for example, by the channel existing in the motor. On the other side then a medium line can be engaged or connected.

Cleverly this is done in such a way that the passage leads from the side opposite the drive or the driven tool or the driven spindle to the side facing the tool. The media, whether they are gas or liquid, or eventually electric lines or the like, here do not serve for the use in or at the motor itself, but they pass the motor, as it were.

This means therefore there are spatially separated units which are provided by solution according to the invention.

The invention comprises here, as already mentioned, a design where the passage in the short circuit body receives one or more medium lines, in the same way as also the modification where the passage forms the medium line. The passage in the short-circuit body is here preferably provided as hose-like channel, as tunnel or as boring for forming or receiving the medium line(s).

The invention suggests furthermore that the medium line(s) serve(s) for supporting and/or operating the elements driven by the electromotor, such as e.g. tools or a spindle. By means of that it is now possible to provide in a space-saving way, for example when it is employed as dental motor, the media required at the tool, such as cooling air, rinsing water which is under high pressure, and, at the same time, to carry out the drive of the tool. The design according to the invention therefore offers the chance of offering a space-saving solution which is in particular highly superior to the solution known in the state of the art when it comes to the comfort of handling. The solutions known in the state of the art which deal exclusively with cooling the electromotor or its stator or rotor are not suited for the case of application as described above.

Compared with that the invention offers a very smart solution which solves cleverly all problems known in the state of the art.

As already mentioned the design of the invention is characterised in that the medium lines are guided from the side opposite the drive side of the electromotor to the side facing the drive through the electromotor. It is, of course, if desired, also possible to select the reverse direction. However, the modification described first is preferred.

The invention is also characterised in that the medium lines are provided as units spatially separated from the motor. By means of that it is possible to pass one or more media through the motor without loading it or reducing its performance essentially. This has already been described before.

In the suggestion according to the invention the medium line is arranged in the electromotor rather far outside. This is convenient as then neither U-bends nor right-angle bends are required in the further course as it is often striven for to employ or provide the medium line (s), for example gas, air, water and so on, with a certain distance to the point of working. On the one hand by this the production of the electromotor according to the invention or the dental tool or instrument driven by it is made easier, and, on the other hand, also the flow characteristics are improved.

Furthermore, the medium guide makes a small air gap in the stator short-circuit plate between rotor and stator possible, and thus a high magnetic flow in the magnetic circuit.

In a preferred modification of the invention a hose-like channel, a tunnel or a boring for forming or receiving the medium line is provided in the short-circuit body.

There is a number of options for the design of the short-circuit body, as it will be explained later on. It is basically possible, that the short-circuit body is designed, for example, sleeve-like and has a boring forming the medium line. The same kind of medium line, however, is produced if the short-circuit body is formed by a number of similarly designed short-circuit discs which have an opening or a rupture at a predetermined position. If these discs are now stapled one above the other the respective openings are positioned at the same point and thus also form a channel, more exactly a hose-like channel or tunnel as in the boring. It is, of course, also possible to form instead of a hose-like channel closed on all sides as medium line also to form consciously a groove or flute in the short-circuit body as medium line. If necessary then, depending on the place where this groove or flute is arranged in the short-circuit body an external sleeve is put on or an interior tube is inserted in order to get thus a sealed medium line. The term "medium line" has to be interpreted very widely, according to the invention. First of all, it is provided, according to the invention, that the boring put in the short-circuit body or the hose-like channel or the tunnel itself forms the medium line, for example as tube, and thus serves as part of the line system for gases or water or other liquids and so on. The hose-like channel, tunnel or the boring, however, may also serve in another modification for receiving another medium line, for example an electric line, a data line (for example of sensors) or a glass fiber cable. The chosen formulation covers both cases.

It is clear that the electromotors according to the invention are, of course, also equipped alternatively with mixed forms of the design of medium lines. The invention comprises here electromotors equipped with only one medium line as well as electromotors equipped with several medium lines. Even if above and in the following often only one medium line is mentioned these statements refer, of course, also in the same way to the arrangements with several medium lines.

Cleverly it has been found that the medium line is arranged diagonally in the short-circuit body, with reference to the rotational axis of the rotational shaft. Such an orientation as well as an also alternatively provided arrangement of the medium line in the short-circuit body on a spiral-shaped or screw-shaped path leads to the improvement of the magnetic behaviour of the short-circuit body or the entire electromotor. Of course, the incorporation of the medium line as material weakening or by removing material in the short-circuit body leads to a corresponding impairing of the magnetic qualities. Bosh moments occur at the electromotor because of the different magnetic qualities of the short-circuit body. However, if now the arrangement of the medium line impairing the magnetic qualities in axial direction is changed the negative effect of the bosh moments is reduced or does not appear at all. For that it is then convenient if the medium line is installed in the short-circuit body along a direction differing from the parallel line of the rotational axis or the rotor shaft. This can be, on the one hand, an arrangement running diagonally to it, or, on the other hand, a spiral-shaped or screw-shaped path which then runs through the short-circuit body like a helix. Here a spiral-shaped path differs from a screw-like path by the changing diameter of the spiral-shaped path compared with the constant diameter of the screw-like path.

Besides these modifications which suppress well an electromotor where the medium line(s) is/are arranged parallel to the rotational axis of the rotor shaft is possible according to the invention. If, for example, the electromotor is only penetrated by one or a few medium line(s) no impairing of both moments may occur during operation.

The short-circuit body has a certain wall thickness and is often shaped like a cylinder or a sleeve. With reference to this wall in a preferred modification of the invention the medium line is arranged in the center and surrounded on all sides by the material of the short-circuit body.

Alternatively to that it is possible that the medium line is arranged in the border area of the short-circuit body on the inside or outside. The invention comprises here also solutions where in the marginal area a boring or a hose-like medium line is provided, or even a groove-like or flute-like design is chosen. This depends, on the one hand, on the desired resulting magnetic properties, but also, on the other hand, on the purpose of the medium line. Thus, for example inserting a beam waveguide as lighting means, or the insertion of an electric cable in a groove or flute is simpler than guiding it through a boring or a tunnel of several centimeters of length. Accordingly mounting is made easier. On the other hand, of course a boring or a hose-like design of the medium line offers a close arrangement from the beginning which is desired, for example, for directing gases or liquids.

It is possible here that the medium line is arranged on the inside, that is the side facing the rotor, or the outside. Of course, mounting on the outside is easier, especially if a groove-like design of the medium line(s) is desired. Both modifications belong to the invention all the same.

In a preferred modification of the invention it is provided that the short-circuit body is designed as sleeve. This sleeve is designed, for example, as lathe work in one piece and has, for example, an axial extending boring, or has a helix-like or diagonally running groove at the surface (interior or exterior surface).

Besides a design of the short-circuit body in one piece as sleeve it is also provided in a development according to the invention that the short-circuit body consists of several combined sleeve segments. The sleeve segments are again possibly similar to each other or even different. The sleeve segments are in contact on their respective front sides and can be linked with each other in a suitable way. The arrangement of sleeve segments has advantages in particular also for incorporating the medium line as these, for example, can be realised at the front sides, for example also by milling out the front side.

In another modification according to the invention it is provided that the short-circuit body consists of a number of short-circuit discs arranged one beside the other in axial direction. A number of essentially identically designed short-circuit discs is combined like a package and has in its respective circumference position in a given way corresponding breaking-outs or ruptures or openings in order to effect thus the medium line(s) or to receive them. Suitable grooves or tunnels are formed across the whole length of the short-circuit body.

Cleverly here the short-circuit disc is designed as stamping so that for example, an economical production is guaranteed, on the one hand, and, on the other hand, the stamped discs can be reproduced with a high repeat degree of the single discs to one another.

The electromotor according to the invention is designed preferably as direct-current motor, in particular for the case of employment for a drive for dental instruments the electromotor according to the invention is designed as collector-less direct-current electromotor.

In a preferred embodiment of the invention it is provided that the medium line(s) serve(s) for the transport of gases such as air, compressed air, cooling air, cleaning gases, liquids, water, liquid gas mixtures, spray water, cooling water, electricity or even light. In particular the development of the beam waveguides allows the employment of beam waveguides and thus to offer a high luminous power by the beam waveguides with a limited space. Here the medium line (groove, tunnel and so on) receives these beam waveguides.

Furthermore the invention comprises not only an electromotor as described in the beginning, but it also refers to a medical or dental tool driven by an electromotor of this type. It has to be taken into consideration here that this case of application is only one of many where the electromotor according to the invention can be employed. In this respect the electromotor does not have to comply with certain dimensions. The electromotor can even be employed in machines which are clearly bigger than a hand-held medical or dental tool. Furthermore the invention comprises also tool motor spindles where an electromotor as described is used as direct drive and through which, for example, a cooling liquid is guided to the machining tool.

Medical or dental tools often have a coupling to which different medical or dental instruments or apparatus can be coupled. This enlarges the field of application of such a tool considerably. Often this type of tools requires the employment of suitable media which have to be approached via medium lines.

BRIEF DESCRIPTION OF THE DIFFERENT VIEWS OF THE DRAWINGS

Figure 2A:
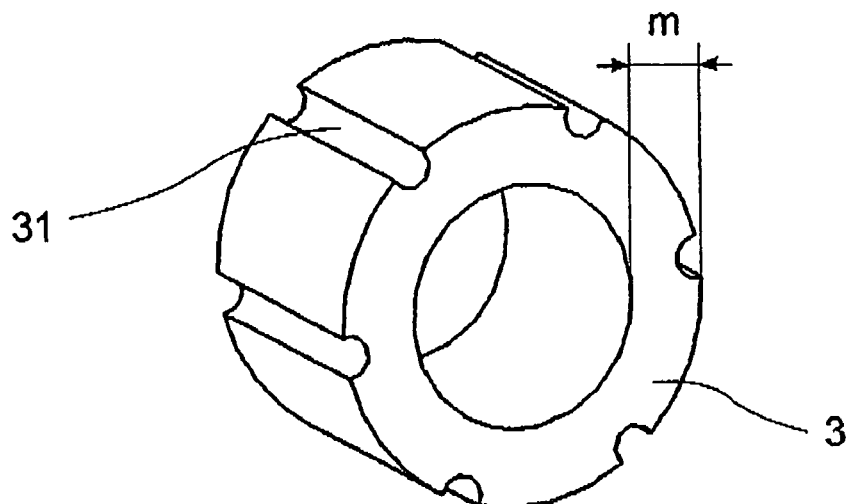
Figure 2B:
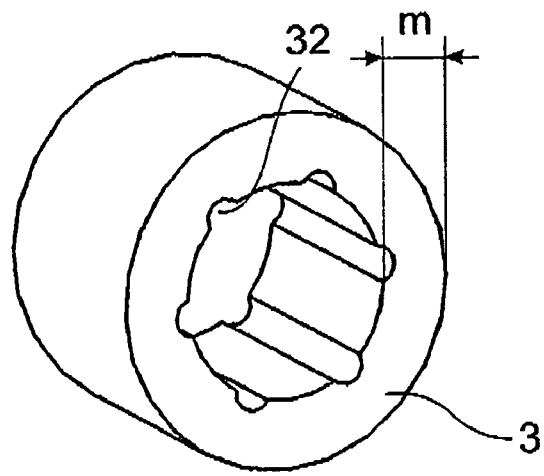
Figure 2C:
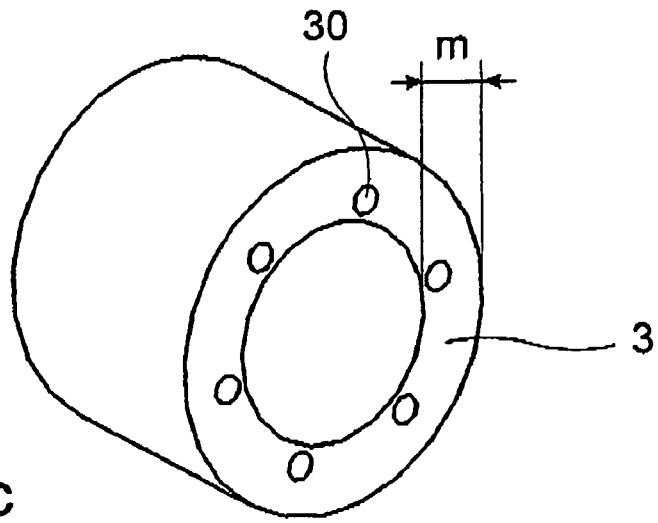
Figure 3:
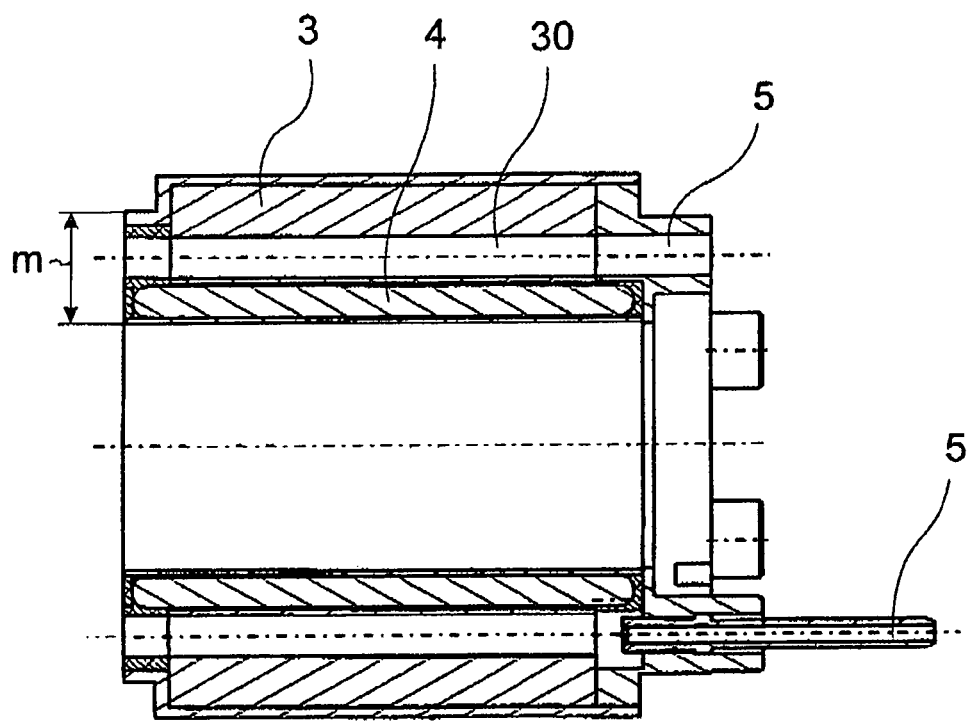

The invention is shown schematically in the drawing. In the drawing:

FIG. 1 in a section in a three-dimensional view an electromotor according to the invention;

FIGS. 2a, 2b, 2c each in a three-dimensional view different embodiments of the short-circuit body according to the invention;

FIG. 3 a section of the electromotor according to the invention and

Figure 4:
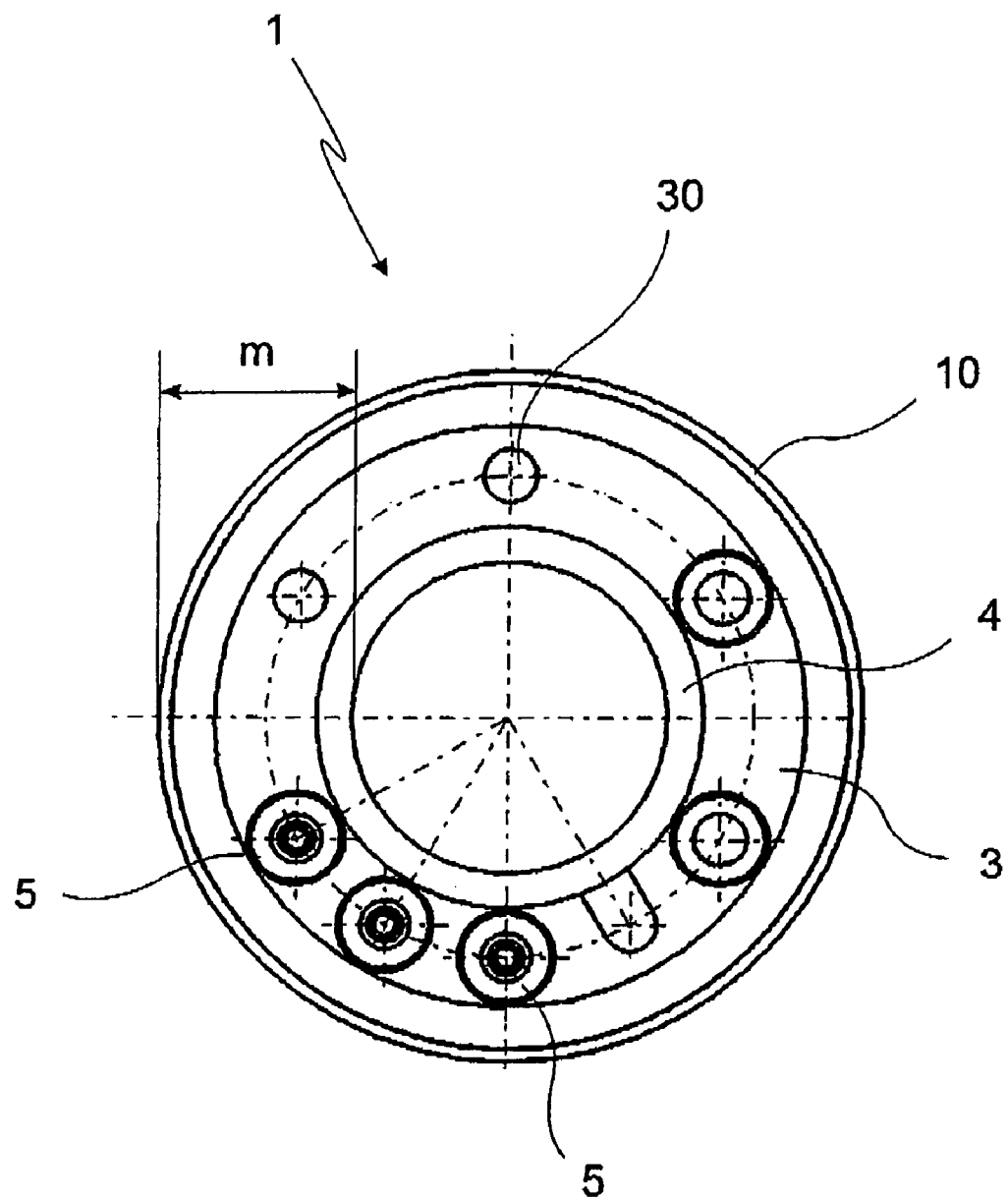

FIG. 4 a top view of the electromotor according to the invention.

DETAILED DESCRIPTION OF THE PREFERRED EMBODIMENT

FIG. 1 shows in a three-dimensional view a part of the electromotor according to the invention. The movable parts of the electromotor as they are rotating are not shown.

Generally, however, the driving parts of the electromotor are arranged in a motor housing, also a coupling part being connected with the housing on which a dental or medical instrument or apparatus which has to be driven by the electromotor can be put. The coupling part is often a standard coupling in order to be exchangeable with other systems.

Furthermore the electromotor 1 has a rotor shaft running on bearings in the motor or motor housing, for that suitable motor bearers are provided in a known way. The rotor (not shown) is surrounded by the stator 2. Stator 2 here consists of a short-circuit body 3 and a winding 4 which can be impinged by current. In a known way the rotor has a permanent magnet which starts rotating because of the magnetic field forming in the winding 4. The permanent magnet of the rotor is here designed as two-pole rotor magnet orientated diametrically. The short-circuit body 3 often consisting of soft magnetic material serves for an effective guide of the magnetic field produced by the winding 4 impinged by current.

In the example shown here the winding 4 is provided on the inside 33 of the short-circuit body 3. In order to protect the winding 4 a protective coat or protective sleeve 40 is provided arranged between winding 4 and the rotor (not shown). This protective sleeve 40 for example designed as protective shell can be, for example, an extrusion of the winding 4. Alternatively it is, of course, also possible to arrange the winding 4 on the outside of the short circuit body 3.

On the front side 11 of the electromotor 1 several medium lines 5 project parallel to the longitudinal extension of the electromotor 1. These medium lines 5 serve, for example, for directing gases, air, water, liquids, current, light and so on.

According to the invention it is suggested that the short-circuit body 3 receives the medium lines 5. In the example shown in FIG. 1 a boring or passage 30 designed as tunnel running to the rotational axis (not shown) of the rotor shaft is provided in which the medium line 5 extends.

The term "medium line" is here to be understood very widely. A medium line is here an independent, closed system for guiding the medium as it is, for example, provided in an electric line which has a suitable insulating extrusion. The term "medium line" 5, however, can also interpreted in that respect that the passage 30 designed as tunnel or the boring or channel 30 or even the grooves 31, 32 themselves are part of the medium line 5 in particular if this is part of a line system for water, liquids, gas and so on.

Just in FIG. 1 the advantage according to the invention becomes clear according to which the already existing width or margin "m" of the short-circuit body 3 is used additionally in order to receive in this short-circuit body the medium line 5. The arrangement of the medium line 5 therefore does not require additional constructive space and does not widen the electromotor 1.

In FIG. 2a an alternative embodiment of the short-circuit body 3 is shown. It consists here of the grooves 31 provided on the outside of the sleeve-like short-circuit body 3.

In FIG. 2b the medium line 5 is provided in grooves 32 provided on the inside. It is obvious that here a number of medium lines can be installed as also a number of grooves is arranged.

The embodiment of the short-circuit body 3 shown in FIG. 2c corresponds with the short-circuit body 3 installed in FIG. 1.

The short-circuit bodies 3 shown in the examples are constructed sleeve-like or cylinder-like without restricting the invention in any way to it. They can be produced in one piece or consist of different sleeve segments or even consist of a number of short-circuit discs combined to a package which are similar or identical to each other.

The design of the short-circuit body 3 is here not necessarily a cylinder-shaped design, in particular the exterior contour of the short-circuit body can be shaped oval or even rectangular.

On the outside of the electromotor 1 a sleeve-like shell 10 is provided which has either a protective purpose for the electromotor or may be also a part of the motor housing.

In FIG. 3 and FIG. 4 the electromotor according to the invention is shown again in two different views. The reference numbers used here follow in an analogous way from FIG. 1.

Although the invention has been described by exact examples which are illustrated in the most extensive detail, it is pointed out that this serves only for illustration, and that the invention is not necessarily limited to it because alternative embodiments and methods become clear for experts in view of disclosure. Accordingly changes can be considered which can be made without departing from the contents of the described invention.

The invention claimed is:

1. Electromotor comprising
a rotor rotatably running on bearings on a rotor shaft and a stator surrounding the rotor,
the stator having a short-circuit body and a winding which can be impinged by current,
at least one medium line,
the short circuit body having at least one passage for at least partly receiving or forming the at least one medium line,
the at least one passage in the short circuit body being a groove or a flute located on a radially inner marginal circumference between opposite ends of the short circuit body for forming or receiving the at least one medium line, the at least one passage terminating at the opposite ends of the short circuit body, and
elements driven by the electromotor being at least one of supported and driven by the at least one medium line.

2. Electromotor according to claim 1, wherein the passage in the short-circuit body is provided as a hose-like channel, tunnel or boring for forming or receiving the at least one medium line.

3. Electromotor according to claim 1, wherein the at least one medium line is guided on a side of the short-circuit body opposite to a driven side.

4. Electromotor according to claim 1, wherein the at least one medium line is provided as units separated spatially in the motor.

5. Electromotor according to claim 1, wherein the passage or the at least one medium line in the short-circuit body is arranged parallel to a rotational axis of the rotor shaft.

6. Electromotor according to claim 1, wherein the short-circuit body is a sleeve.

7. Electromotor according to claim 1, wherein the short-circuit body includes several combined sleeve segments.

8. Electromotor according to claim 1, wherein the short-circuit body includes a number of short-circuit discs arranged one beside the other in an axial direction.

9. Electromotor according to claim 1, wherein the short-circuit body includes a number of short-circuit discs arranged one beside the other in an axial direction, and the short-circuit discs are stampings, in recesses forming the passage or a channel or a tunnel or a groove.

10. Electromotor according to claim 1, further comprising a collector-less direct current motor.

11. Electromotor according to claim 1, further comprising a medical or dental instrument.

12. Electromotor according to claim 1, wherein the at least one medium line also serves for transporting gas, liquid, current, data or light.

13. Electromotor according to claim 1, wherein the winding has a protective shell or protective coating.

14. Medical or dental tool which is driven by an electromotor according to claim 1.

15. Tool motor spindle with an electromotor according to claim 1 as a drive of the tool.

* * * * *